United States Patent [19]
Teramachi et al.

[11] Patent Number: 5,569,605
[45] Date of Patent: Oct. 29, 1996

[54] ORGANIC WASTE DISPOSAL SYSTEM

[75] Inventors: Masayoshi Teramachi, Nagoya; Kinichi Kinoshita, Mie-ken; Yosihito Takakuwa, Nagoya; Eiji Fukui, Aichi-ken; Tadashi Kamiyanagita, Mie-ken, all of Japan

[73] Assignees: The Chubu Electric Power Co., Inc., Nagoya; Kabushiki Kaisha Toyodynam, Aichi-ken, both of Japan

[21] Appl. No.: 353,441

[22] Filed: Dec. 9, 1994

[30] Foreign Application Priority Data

Dec. 16, 1993 [JP] Japan ................... 5-344324

[51] Int. Cl.⁶ ........................................... C05F 9/02
[52] U.S. Cl. ............................ 435/290.2; 435/290.4
[58] Field of Search ........................ 435/290.1, 290.2, 435/290.4; 71/8–10

[56] References Cited

U.S. PATENT DOCUMENTS 2,878,112  3/1959  Morrison ................. 435/290.4
3,577,229  5/1971  Bruck ..................... 435/290.4
4,062,770  12/1977 Kneer ..................... 435/290.1
4,483,704  11/1984 Easter .................... 435/290.4
4,882,058  11/1989 Burton .................... 435/290.4

*Primary Examiner*—William Beisner
*Attorney, Agent, or Firm*—Flynn, Thiel, Boutell & Tanis, P.C.

[57] ABSTRACT

An organic waste disposal system capable of speeding up drying and fermenting speeds and of continuously treating raw materials, and furthermore capable of operating in a clean working environment and reducing a running cost. The organic waste disposal system has a crusher for changing the organic wastes into flowing material, a preparatory fermentor including an agitating blade wherein the crusher and the preparatory fermentor are connected by a pump, and it further has a fermentor with a heating mechanism and a plurality of agitating blades. A hot air circulation pipe, on which a water heater utilizing accumulated heat and dehumidifier, is provided. The preparatory fermentor and the fermentor are both connected to the pump. A suction portion of a cyclone having a suction function is connected to the fermentor by a suction pipe. Each device of the system set forth above, is connected to a deodorizer.

9 Claims, 8 Drawing Sheets

ORGANIC WASTE DISPOSAL SYSTEM

BACKGROUND OF THE INVENTION

1. Field of the Invention

The present invention relates to an organic waste disposal system including fermentation process (hereinafter referred to as organic waste disposal system) for automating a continuous disposal of organic wastes, which operates from the introduction of organic wastes to carrying out of the disposed organic wastes.

2. Prior Art

A fermenting apparatus, having a fermentor, agitating blades and heater respectively housed in the fermentor, has been conventionally used for disposing of organic wastes such as garbage, sludge, animal residue, etc.

However, such a fermenting apparatus has the following drawbacks.

Since the organic wastes to be introduced into the fermenting apparatus contains solid material therein, fermenting efficiency is very low and inner malodorous gas is leaked outside when an introduction door is opened, thereby deteriorating working environment. Furthermore, although the disposed wastes are taken out by an exhaust port when reversely rotating the agitating blades, particles are liable to be diffused outside the apparatus since the disposed wastes are dried and changed into fine particles in the fermentor, which also deteriorates the working environment. Still furthermore, it is only possible to perform a batch disposal, namely, dispose of a given amount of wastes, but impossible to continuously dispose of the wastes.

SUMMARY OF THE INVENTION

It is an object of the present invention to provide an organic waste disposal system capable of keeping raw materials temporarily in a preparatory fermentor and continuously disposing of the treated wastes, thereby enhancing and cleaning the work environment and reducing the operating costs involved in the disposing of the wastes by utilizing circulation of exhaust air and accumulated heat energy.

In view of the drawbacks of the prior art fermenting apparatus, namely, deterioration of the working environment and noncontinuous disposal of the wastes, the organic waste disposal system according to the present invention has a crusher, a primary or preparatory fermentor (hereinafter referred to as a preparatory fermentor), a secondary fermentor (hereinafter referred to as simply as fermentor), a cyclone and a deodorizer, wherein the crusher crushes the organic wastes, including the solid material, resulting in a flowing material, and the flowing material is introduced into the preparatory fermentor by a pump.

With such an arrangement, continuous introduction of raw waste material can be performed by providing a preparatory fermentor for temporarily storing the raw waste material therein between the crusher and the fermentor, and malodor can be deodorized by using a closed system, namely, by connecting all of the devices to a deodorizer, in which heat energy accumulated in a water heater of the fermentor can be effectively utilized.

The preparatory fermentor has an agitating blade which agitates the introduced raw material. It then preparatorily ferments the introduced raw material. The preparatorily fermented material is purged into the fermentor.

The fermentor has agitating blades for agitating the preparatorily fermented material, an electric heater, and a water heater for utilizing accumulated heat energy effectively. A dehumidifier is connected to a hot air circulation pipe for dehumidifying the hot air while reducing heat energy loss.

A cyclone separator sucks the treated material, as powdered fine particles together with malodorous gas, from the fermentor via a suction port connected to the fermentor and separates the malodorous gas from the treated material. The deodorizer is connected to the crusher, the preparatory fermentor, the fermentor, and the cyclone separator, for vacuuming and deodorizing the malodorous gases generated in these devices and then exhausts the deodorized malodorous gas outside of the system.

PREFERRED EMBODIMENT OF THE INVENTION

Figure 1:
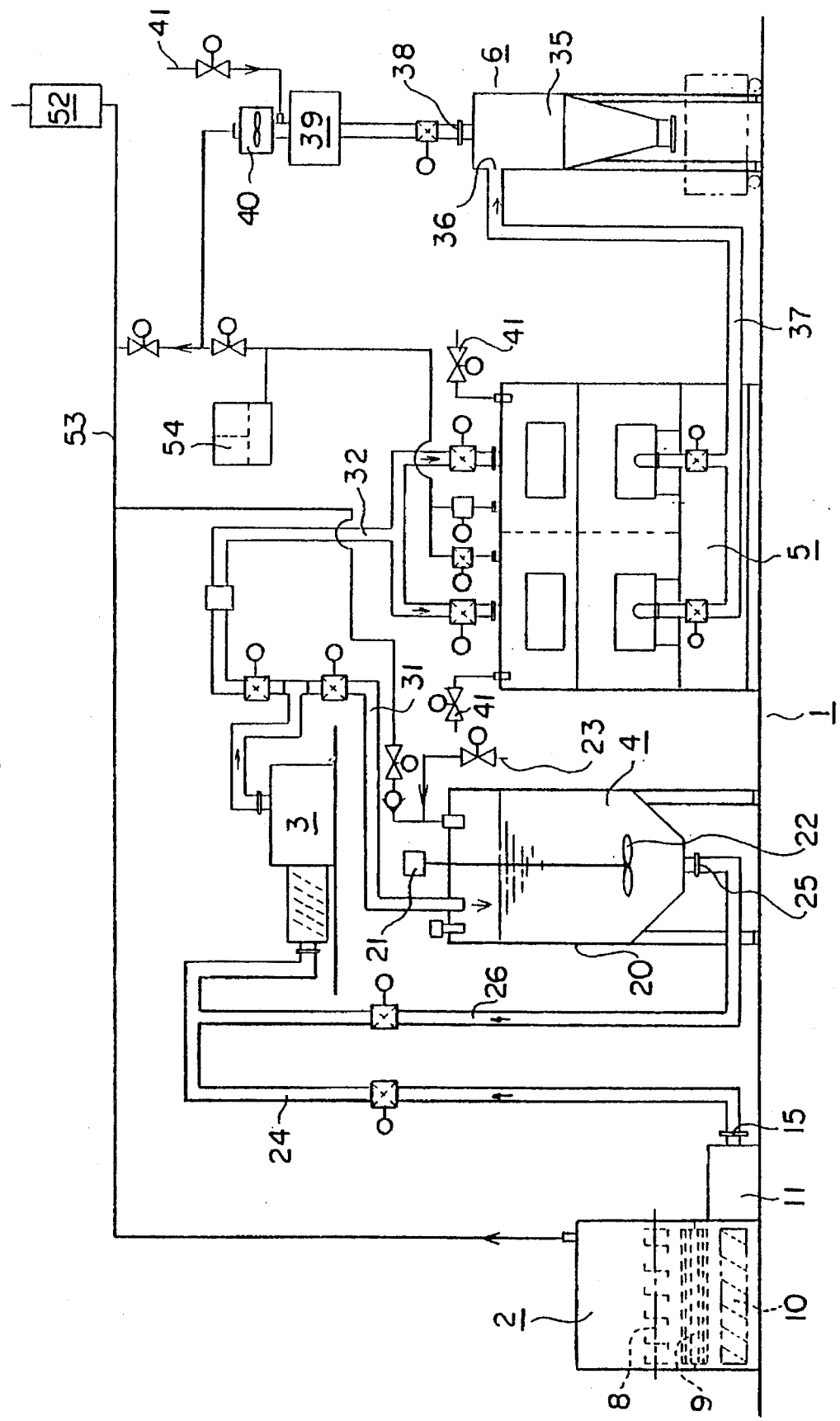
FIG. 1 is a view showing generally an organic waste disposal system according to a preferred embodiment of the present invention.
Figure 2:
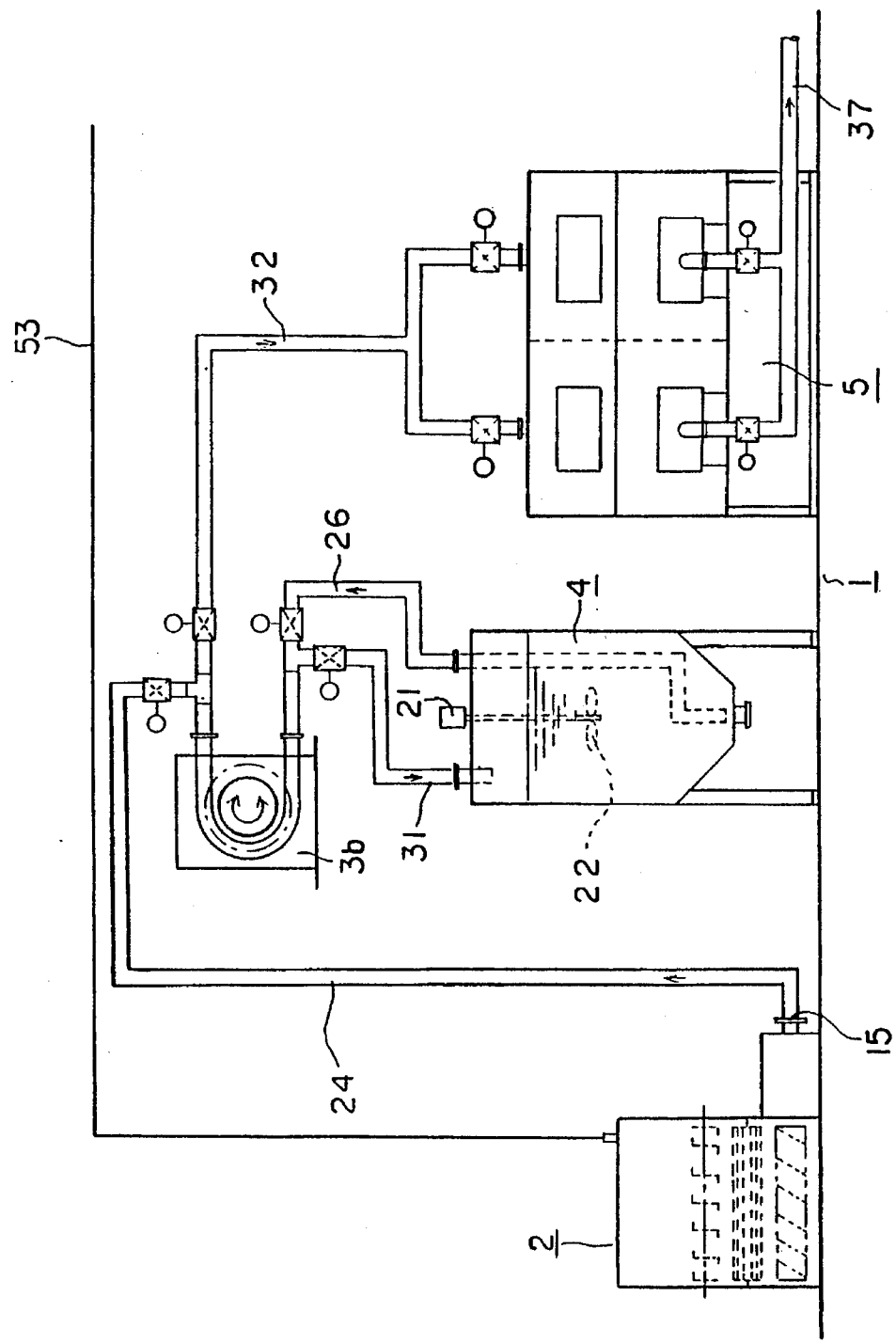
FIG. 2 is a view showing generally an organic waste disposal system having a modified pump according to the present invention.
Figure 3:
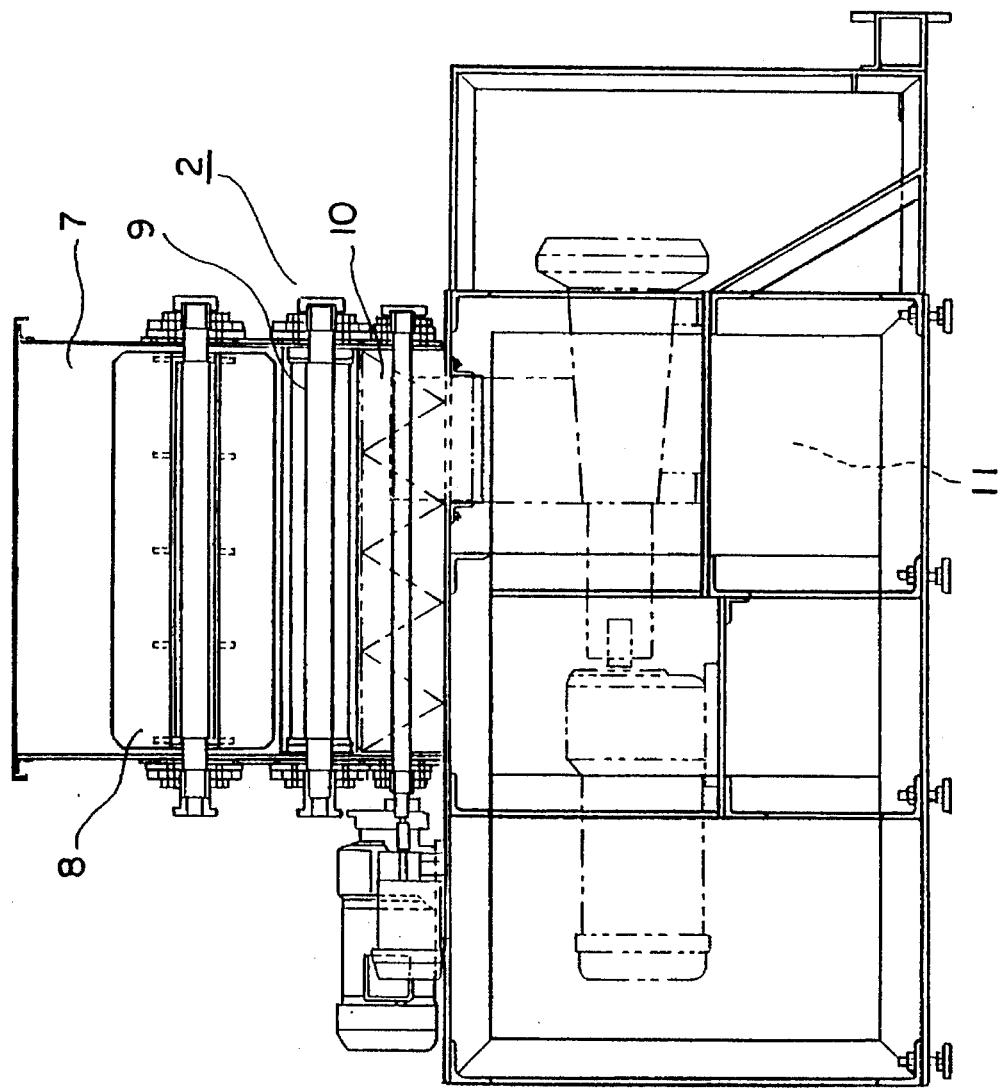
FIG. 3 is a cross-sectional view of a crusher as shown in FIG. 1.
Figure 4:
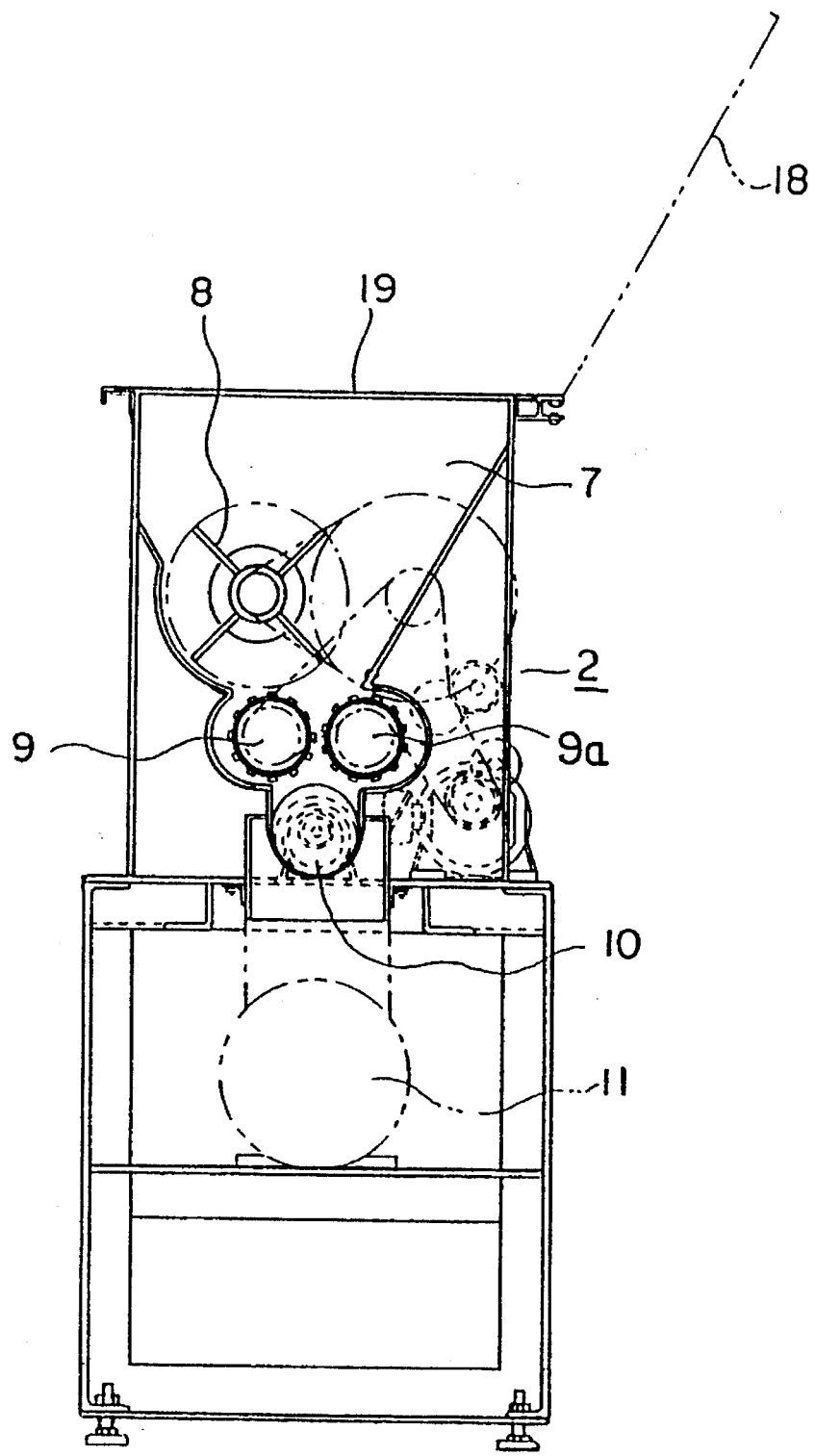
FIG. 4 is a cross-sectional view of a crusher as shown in FIG. 1 viewed from another aspect.
Figure 5:
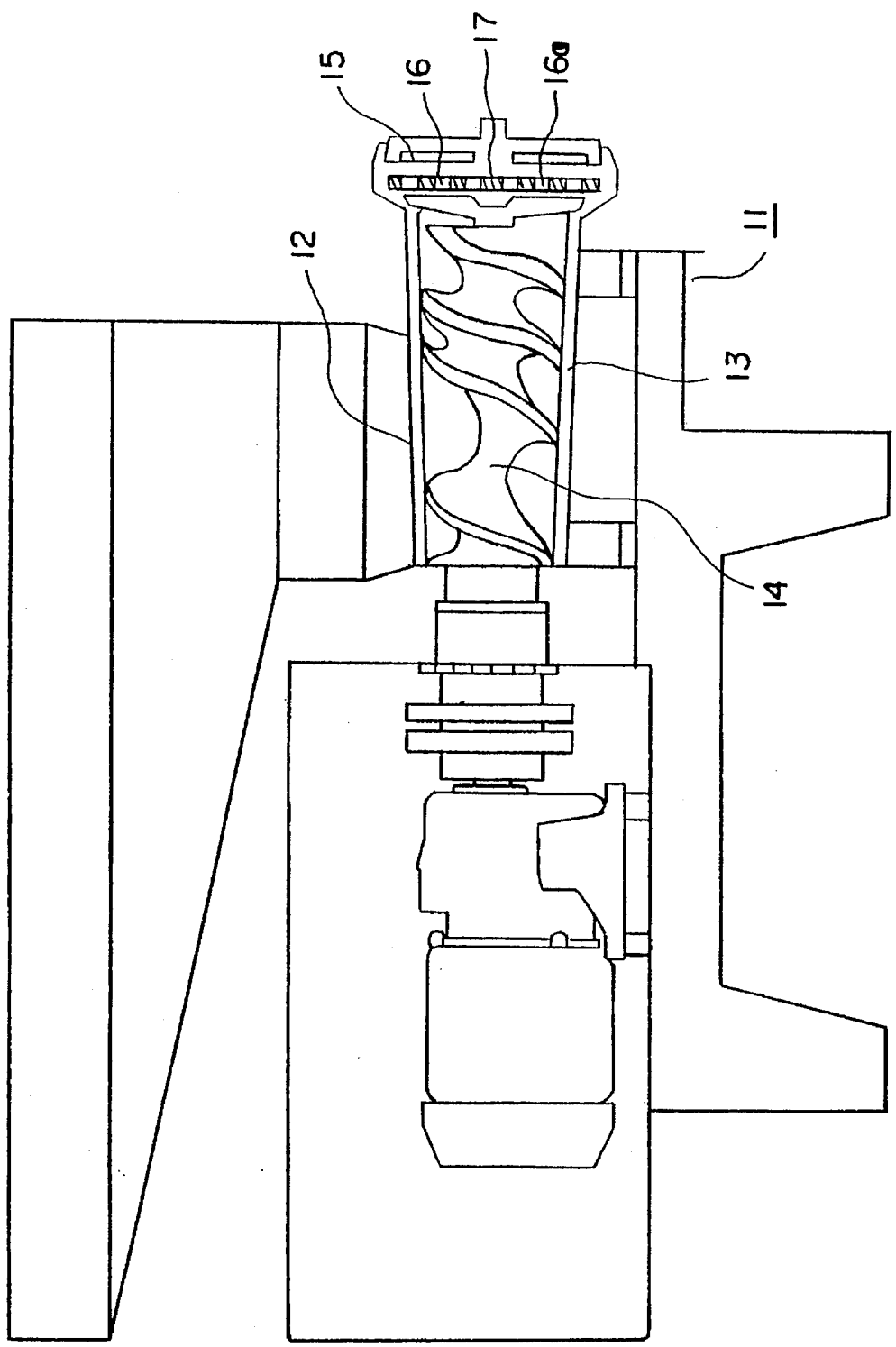
FIG. 5 is a partly cut-away cross-sectional view of an extruder of the crusher as shown in FIG. 1.

An organic waste disposal system according to a preferred embodiment will be described with reference to FIGS. 1 to 8.

The organic waste disposal system 1 has a crusher 2 for crushing raw material of organic wastes including solid materials such as garbage, sludge, animal residue, etc., a pump 3 for transferring flowing material, a preparatory fermentor 4 for preparatorily fermenting the crusted and granulated material, a fermentor 5 for fermenting and drying the preparatorily fermented material and an exit unit 6 for disposal of the dried treated material.

The crusher 2 has a hopper 7 into which the raw material is introduced, squeezing blades 8 for squeezing the raw material downward, crushing rollers 9 and 9a disposed under the squeezing blades 8, and a screw conveyor 10 disposed under the crushing rollers 9 and 9a.

An extruder 11 is disposed under the screw conveyor 10 and has a cylindrical barrel portion 13 which has an introduction port 12 connected to the screw conveyor 10. An extrusion screw 14 is provided inside the barrel portion 13. An exhaust opening 15 is provided at the tip end of the extrusion screw 14, and a discharge plate 17 is provided at the exhaust opening 15 having a plurality of discharge apertures 16, 16a, bored therein.

The hopper 7 has a closable cover 18 attached to an upper entry port 19 thereof.

The pump 3 is a rotary volume type Mono pump 3a with one axle eccentric screw pump for delivering a given amount of material without pulsation, or is a squeeze type tube pump 3b for delivering the material by squeezing thereof in the tube.

The preparatory fermentor 4 has a cubic airtight container 20 in which an agitating blade 22 connected to a motor 21 is disposed and which is connected at the upper portion thereof to a compressed air supply pipe 23 connected to a compressed air supply source, not shown.

Although the compression air supply pipe 23 is connected to the upper portion of the container 20, it is not limited thereto. For example, it can be disposed in the flowing material contained in the container 20 so as to subject the flowing material to an aeration process.

A suction side of the Mono pump 3a and the exhaust opening 15 of the extruder 11 of the crusher 2 are connected to each other by way of a raw material suction pipe 24 having a closable valve through which the flowing material is permitted to flow from the crusher 2 to the Mono pump 3a. The suction side of the Mono pump 3a and a exhaust port 25 disposed at the lower end of the container 20 of the preparatory fermentor 4 are connected to each other by way of a preparatorily fermented material suction pipe 26 having a closable valve through which the preparatorily fermented material is permitted to flow from the preparatory fermentor 4 to the Mono pump 3a.

The fermentor 5 has a lateral type airtight fermenting container 27. A rotary shaft 29 connected to a motor 28 is disposed in the fermenting container 27 in the lateral direction and a plurality of agitating blades 30 extend radially from the rotary shaft 29 so as to agitate the preparatorily fermented material which is supplied to the fermenting container 27.

A discharge side of the Mono pump 3a and the container 20 of the preparatory fermentor 4 are connected to each other by way of a raw material supply pipe 31 having a closable valve, through which the raw material is permitted to flow from the Mono pump 3a to the preparatory fermentor 4. The discharge side of the Mono pump 3a and the fermenting container 27 of the fermentor 5 are connected to each other by way of a preparatorily fermented material supply pipe 32 having a closable valve through which the preparatorily fermented material is permitted to flow from the Mono pump 3a to the fermentor 5.

A piping of the tube pump 3b for transferring the raw material or the preparatorily fermented material is structured in the manner that one connection side of the tube pump 3b is connected to the exhaust opening 15 of the extruder 11 of the crusher 2 by way of the fermented material suction pipe 24 and also connected to the upper portion of the fermenting container 27 of the fermentor 5 by way of the preparatorily fermented material supply pipe 32. The other connection side of the tube pump 3b is connected to the upper and lower portions of the container 20 of the preparatory fermentor 4 by way of the raw material supply pipe 31 and the preparatorily fermented material suction pipe 26.

Figure 6:
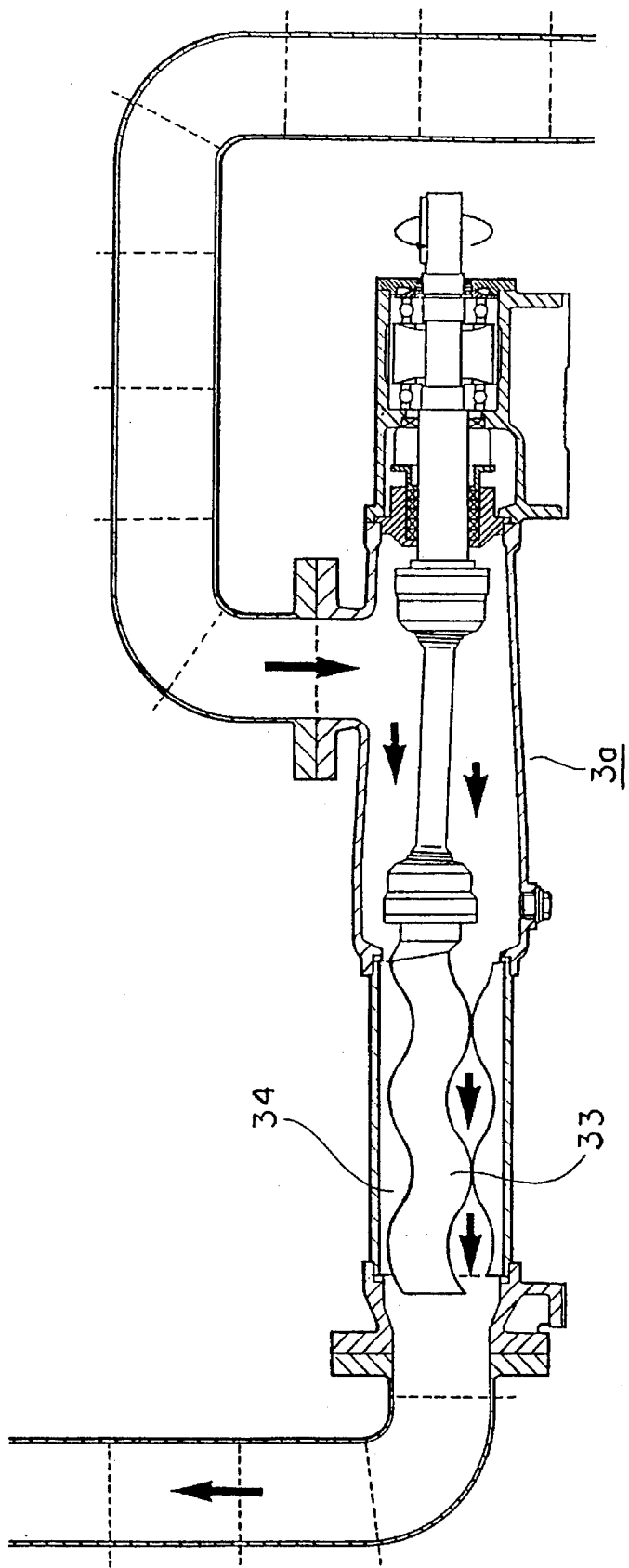
FIG. 6 is a cross-sectional view of a Mono pump as shown in FIG. 1.
Figure 7:
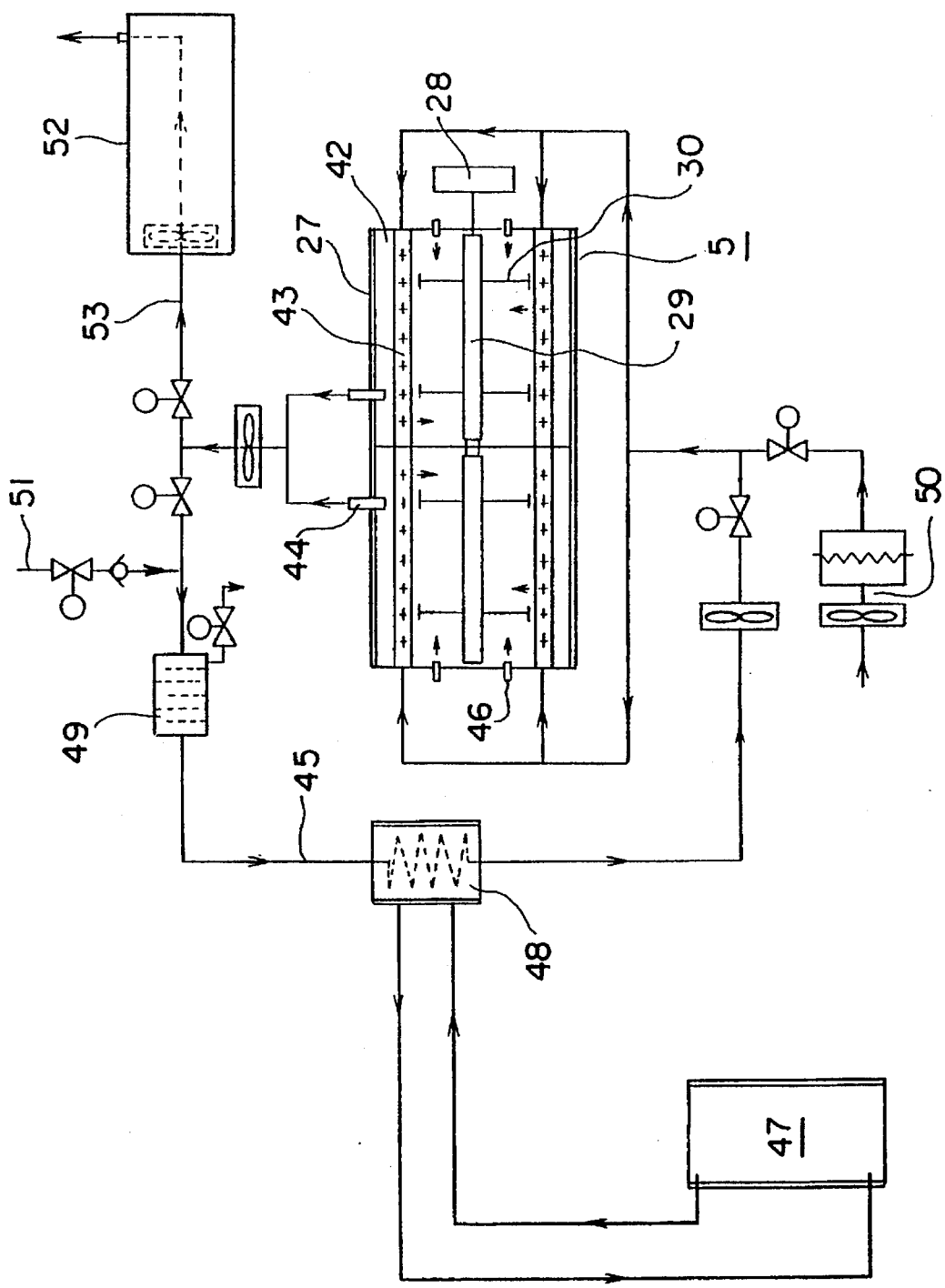
FIG. 7 is view showing a wet air circulation route in a fermentor as shown in FIG. 1.
Figure 8:
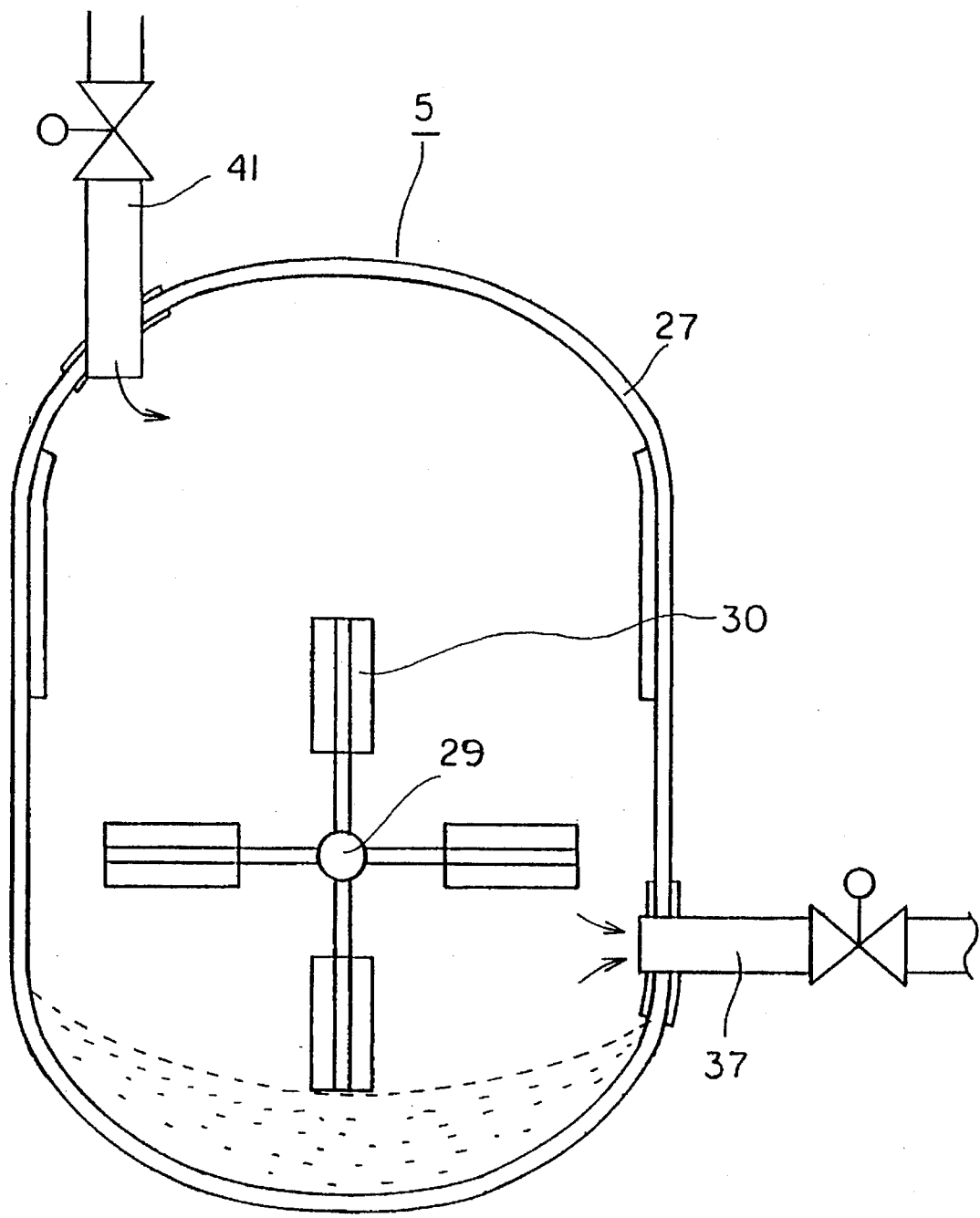
FIG. 8 is a view showing the state when treated material is sucked from the fermentor as shown in FIG. 1.

In FIG. 6, the Mono pump 3a has a rotor 33 which is completely round in cross section and formed of a male screw rotor, and a stator which is elliptic in cross section and formed of a female screw. The rotor 33 reciprocates inside the stator 34 while rotating when the rotor 33 is rotated about the center of an eccentric shaft.

The exit unit 6 has a cyclone separator 35 having a suction port 36 at the upper portion thereof which is connected to the lower portion of the fermenting container 27 by way of a disposed material suction pipe 37 having a closable valve through which the disposed material is permitted to flow from the fermentor 5 to the exit unit 6.

An exhaust pipe 38 provided above the cyclone 35 is connected to a bag filter 39 and the bag filter 39 is connected to a blower 40. A fresh air introduction port 41 is connected to a communication passage between the bag filter 39 and the blower 40 and it is closable by a valve.

A heating mechanism of the fermentor 5 in the hot air circulation route has a sheet-shaped electric heater 42 provided at the inner periphery of the fermenting container 27 and is heated by electricity, hot air jetting pipes 43 and exhaust pipes 44 which are respectively provided inside the fermenting container 27 and are connected to a hot air circulation pipe 45. Duct heaters 46 are also provided in the fermenting container 27.

A heat exchanger 48 is connected to a water heater 47 which utilizes midnight generated power to reduce costs, a dehumidifier 49 and a hot air supply unit 50 which also utilizes midnight generated power, are respectively connected to the hot air circulation pipe 45. A fresh air introduction port which is closable by a valve is connected to the hot air circulation pipe 45.

A deodorizer 52 has a suction function and is connected by way of a deodorizing pipe 53 to the crusher 2, the preparatory fermentor 4, the fermentor 5 and the exit unit 6, which all respectively generate malodor. The deodorizer 52 deodorizes the malodor by biologically utilizing microorganisms physically by utilizing adsorbate such as active carbon, etc., and chemically by utilizing ozone, ion, etc.

An adjusting agent storage unit 54 is connected to a deodorizing pipe 53 provided between the deodorizer 52 and the fermentor 5 for introducing dried bean curd lees, i.e. residue left after making tofu, fermented dried disposed material, etc., adjusting agent for adjusting C/N ratio, pH, etc., thereby adjusting water content, etc. of the preparatorily fermented material.

An operation of the organic waste disposal system according to the present invention will be described hereinafter.

When the closable cover 18 of the crusher 2 is first opened so as to introduce the raw material and aerobic ferment bacteria from upper entry port 19 of the hopper 7, the raw material is pushed into and crushed between the crushing rollers 9 and 9a by the squeezing blades 8 in the hopper 7. Thus crushed raw material is supplied to the screw conveyor 10 and is then introduced by the screw conveyor 10 into the barrel portion 13 of the extruder 11 through the introduction port 12. When introduced into the barrel portion 13, the raw material is extruded by the extrusion screw 14 and then discharged through the exhaust apertures 16, 16a, . . . of the exhaust plate 17 as the flowing material.

Since the deodorizer 52 and the crusher 2 are connected to each other by way of the deodorizing pipe 53, when the raw material is introduced into the crusher 2, the deodorizing suction operation is always performed so that the malodorous gas is not exhausted to the outside from the upper entry portion 19 of the hopper 7 even if the closable cover 18 is opened.

The flowing material is introduced into the preparatory fermentor 4 through the pump 3 and is agitated for a given time in the preparatory fermentor 4 by the agitating blade 22, the rotation of which is controlled by the motor 21, and then it is preparatorily fermented and kept in the preparatory fermentor 4 while the air necessary for fermentation is supplied to the preparatory fermentor 4 by way of the compressed air supply pipe 23.

Successively, the preparatorily fermented material, which is stored in the preparatory fermentor 4, is introduced into the fermentor 5 by way of the preparatorily fermented material supply pipe 32, then it is fermented and dried while it is agitated by the agitating blades 30 when the rotary shaft 29 is rotated by the motor 28.

The fermentation process is usually performed at the temperature of about 60° C. If the preparatorily fermented material introduced into the fermenting container 27 of the fermentor 5 has very high water content, water adjusting agent is introduced into the fermenting container 27 from the adjusting agent storage unit 54 or the water content is adjusted by the dehumidifier 49 so as to be in the range from 55 to 65% which is the optimum value for fermentation. At the same time the heat energy accumulated in the water heater 47, which utilized the midnight generated power, is released during the daytime to the air which moves inside the hot air circulation pipe 45 by way of the heat exchanger 48 to change the air into the hot air which is supplied to the fermenting container 27 through the hot air jetting pipes 43 so as to increase the temperature of the preparatorily fermented material to a given value.

The dehumidifier 49 is operated during fermentation so as to perform low temperature drying operation, namely, to reduce the water content of the preparatorily fermented material to 30%, at which level the fermenting bacteria does not perish.

When storing the fermented disposed material for a long time when the fermentation is completed during the time when the midnight generated power is not utilized, a drying process is needed. In the drying process, hot air is supplied from the hot air jetting pipes 43 to the fermenting container 27 by way of the hot air supply unit 50 while stopping the operation of the hot air circulation pipe 45, and the electric heater 42 is operated utilizing the midnight generated power to thereby heat the inside of the fermenting container 27 while agitating the fermented disposed material by the agitating blades 30 and drying the fermented disposed material at high agitating efficiency.

In such a drying process, a part of the air including a malodor is introduced into the deodorizer 52 by way of the deodorizing pipe 53 and is deodorized in the deodorizer 52, then discharged outside.

The fermented treated material is removed as follows upon completion of the drying process. The powdered fermented disposed material in the fermenting container 27 is sucked together with air by the suction port 36 of the cyclone 35 by way of the disposed material suction pipe 37 while it is agitated by the agitating blades 30 in the fermenting container 27. The treated material is discharged from the lower portion of the cyclone 35 and is removed, while the fine particles and air including malodor are exhausted from the exhaust port of the cyclone 35 and is removed by the bag filter 39, then introduced into the deodorizer 52 where the malodor is changed into odorless smell and exhausted outside.

According to the present invention, the crusher 2 for crushing the organic wastes including the solid material to be thereby changed into the flowing material and the preparatory fermentor 4 having the agitating blade are connected to each by way of the pump 3 for transferring the flowing material. Furthermore, the preparatory fermentor 4 and the fermentor 5 having the heating mechanism and the plurality of agitating blades 30 are connected to each other by way of the pump 3. The suction port 36 of the cyclone 35 and the fermentor 5 are connected to each other. As a result of this structure, the solid raw material, such as the raw fish and the bones thereof, is crushed to fine particles so that the surface area of the raw material is increased and the size of the particles is uniform and, moreover, the contact efficiency between the raw material and the air is improved in the drying and fermenting processes, thereby speeding up the drying and fermenting speeds.

Since the raw material is introduced from the crusher 2 into the preparatory fermentor 4 or the preparatorily fermented material is introduced from the preparatory fermentor 4 to the fermentor 5 by the single pump 3, a plant investment cost can be reduced. Furthermore, since the raw material can be continuously introduced into the crusher 2, it is possible to dispose of the raw material continuously from the fermenting process to the drying process. Still furthermore, since the disposed material in the fermentor 5 is sucked by the suction port 36 of the cyclone 35 while it is agitated by the agitating blades 30 in the fermentor 5, the disposed material can be removed and a clean working environment maintained.

Since the deodorizer 52 having the suction function is connected to the crusher 2, the fermentor 5, the exit unit 6 and the cyclone separator 35, all the malodor generated in these devices can be removed by the deodorizer 52. Furthermore, since the deodorizer 52 sucks the malodor even at the time when the raw material is introduced into the crusher 2, the malodorous gases can be prevented from leaking outside the system. Still furthermore, since the malodorous gas separated by the cyclone 35 is sucked by the deodorizer 52, all the processes ranging from the introduction of the raw material to the discharge of the fermented disposed material can be cleaned and deodorized.

Since the heating mechanism of the fermentor 5, which includes the electric heater 42 and is provided at the inner periphery of the fermenting container 27, the hot air jetting pipes 43, and the exhaust pipes 44, which are respectively provided inside the fermentor 5, are connected to the hot air circulation pipe 45, and the heat exchanger 48 connected to the water heater 47 and the dehumidifier 49 are provided on the hot air circulation pipe 45, the heat energy can be accumulated in the water heater 47. If the heat energy can be obtained by utilizing the midnight generated power, the running cost of this organic waste disposal system can be reduced. Furthermore, the water content of the air of high temperature and high humidity can be removed by the dehumidifier 49 in the course of circulation of this air, which highly contributes to the practical effect such as reduction of heat to be lost outside the system and thus save energy.

What is claimed is:

1. An organic waste disposal system comprising:
   a crusher for crushing organic wastes, including any solid waste material into a flowing waste material,
   a preparatory fermentor including an agitating blade;
   a pump having an entrance and an outlet, said pump entrance being connected by a first pipe to said crusher and said pump outlet being connected by a second pipe to said preparatory fermentor for transferring the flowing waste material, said pump entrance being connected to an outlet of said preparatory fermentor by a third pipe;
   a main fermentor having a heating means and a plurality of agitating blades, said main fermentor being connected to said pump outlet by a fourth pipe;
   a cyclone separator for removing material from air having a suction port for receiving treated fermented material laden air from said main fermentor, and said suction port of said cyclone separator being connected to said main fermentor by a fifth pipe.

2. The organic waste disposal system according to claim 1, further comprising a deodorizer for deodorizing air and connected to said crusher, said preparatory fermentor, said main fermentor and said cyclone separator.

3. The organic waste disposal system according to claim 2, wherein an exhaust pipe connects said cyclone separator to a filter, a blower means connects said filter and said deodorizer, and a valve closable air introduction port is connected between said filter and said blower means.

4. The organic waste disposal system according to claim 1, further comprising a heat exchanger, a dehumidifier and a water heater, wherein said heating means comprises an electric heater provided at an inner periphery of said main fermentor and connected to hot air jetting pipes and exhaust pipes, which are respectively provided inside said main fermentor, by a hot air circulation pipe, and wherein said heat exchanger is connected to said water heater and said dehumidifier which are respectively connected to said hot air circulation pipe.

5. The organic waste disposal system according to claim 1, wherein said heating means comprises an electric heater provided at an inner periphery of said fermentor.

6. The organic waste disposal system according to claim 1, wherein said pump is a rotary screw type pump.

7. The organic waste disposal system according to claim 1, herein said pump is a squeeze tube-type pump wherein said squeeze tube-type pump delivers material by sequentially squeezing a tube to force material through said tube.

8. The organic waste disposal system according to claim 1, wherein said first pipe and said third pipe join into a single pipe prior to connecting to said pump.

9. The organic waste disposal system according to claim 1, wherein said first, second, third and fourth pipes have control valves located therein.

* * * * *

UNITED STATES PATENT AND TRADEMARK OFFICE
CERTIFICATE OF CORRECTION

PATENT NO. : 5 569 605
DATED : October 29, 1996
INVENTOR(S) : Masayoshi Teramachi et al It is certified that error appears in the above-indentified patent and that said Letters Patent is hereby corrected as shown below:

```
Column 6, line 52; after "material" (first occurrence)
                   insert ---,---.
Column 7, line 10; change "valve closable" to
                   ---valve-closable---.
```

Signed and Sealed this

Eleventh Day of March, 1997

Attest:

BRUCE LEHMAN

*Attesting Officer*    *Commissioner of Patents and Trademarks*